(12) United States Patent
Lohray et al.

(10) Patent No.: US 7,994,322 B2
(45) Date of Patent: Aug. 9, 2011

(54) PROCESSES FOR THE PREPARATION OF DIFFERENT FORMS OF (S)-(+)-CLOPIDOGREL BESYLATE

(75) Inventors: Braj Bhushan Lohray, Bujarat (IN); Vidya Bhushan Lohray, Gujarat (IN); Bipin Pandey, Gujarat (IN); Mayank Ghanshyambhai Dave, Gujarat (IN); Parind Narendra Dholakia, Gujarat (IN)

(73) Assignee: Cadila Healthcare Limited, Gujarat (IN)

( * ) Notice: Subject to any disclaimer, the term of this patent is extended or adjusted under 35 U.S.C. 154(b) by 0 days.

(21) Appl. No.: 12/065,386

(22) PCT Filed: Aug. 28, 2006

(86) PCT No.: PCT/IN2006/000322
§ 371 (c)(1), (2), (4) Date: Aug. 11, 2008

(87) PCT Pub. No.: WO2007/052300
PCT Pub. Date: May 10, 2007

(65) Prior Publication Data
US 2009/0221827 A1    Sep. 3, 2009

(30) Foreign Application Priority Data
Sep. 5, 2005  (IN) .................... 1072/MUM/2005

(51) Int. Cl.
*C07D 495/04* (2006.01)
(52) U.S. Cl. ....................................................... 546/114
(58) Field of Classification Search ................... 546/114
See application file for complete search history.

(56) References Cited

U.S. PATENT DOCUMENTS
2007/0249660 A1 * 10/2007 Weber et al. ................. 514/301

FOREIGN PATENT DOCUMENTS
| WO | 2004/072084 | 8/2004 |
| WO | 2004/072085 | 8/2004 |
| WO | 2004/106344 | 12/2004 |
| WO | 2005/080890 | 9/2005 |

OTHER PUBLICATIONS
International Search Report for PCT/IN2006/00322, mailed May 15, 2007.

* cited by examiner

*Primary Examiner* — Patricia Morris
(74) *Attorney, Agent, or Firm* — Nixon & Vanderhye P.C.

(57) ABSTRACT

Disclosed herein are the improved processes for the preparation of different forms of (S)-(+)-Clopidogrel besylate, pharmaceutical compositions containing them and their use in medicine.

2 Claims, No Drawings

PROCESSES FOR THE PREPARATION OF DIFFERENT FORMS OF (S)-(+)-CLOPIDOGREL BESYLATE

This application is the U.S. national phase of International Application No. PCT/IN2006/000322, filed 28 Aug. 2006, which designated the U.S. and claims priority to IN 1072/MUM/2005, filed 5 Sep. 2005, the entire contents of each of which are hereby incorporated by reference.

FIELD OF INVENTION

The present invention relates to an improved processes for the preparation of different forms of (S)-(+)-Clopidogrel besylate, pharmaceutical compositions containing them and their use in medicine.

TECHNICAL BACKGROUND

Clopidogrel has the following structure (1)

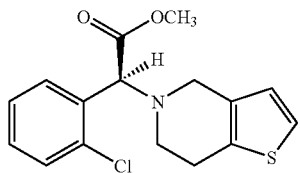

(I)

It is available in the market as its bisulfate salt and is marketed by Sanofi-Synthelabo as "Plavix" having the general formula (II)

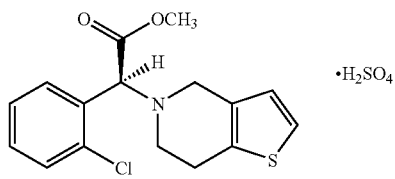

(II)

Clopidogrel is an inhibitor of platelet aggregation and is marketed as an antianginal agent, antiplatelet agent and is found to decrease morbid events in people with established atherosclerotic cardiovascular disease and cerebrovascular diseases.

The therapeutic application of Clopidogrel as blood-platelet aggregation inhibiting agents and antithrombotic agent and its preparation is disclosed in U.S. Pat. No. 4,529,596. U.S. Pat. No. 4,847,265 describes the process for the preparation of the hydrogen sulfate salt of Clopidogrel.

Polymorphs of Clopidogrel bisulfate has been described in U.S. Pat. Nos. 6,504,040 and 6,429,210. We have disclosed novel polymorphs of Clopidogrel bisulfate in our published application WO2004081016.

U.S. Pat. No. 4,847,265 discloses that the dextrorotatory enantiomer of formula (I) of Clopidogrel has an excellent antiaggregant platelet activity, whereas the corresponding levorotatory enantiomer of (I) is less tolerated of the two enantiomers and is less active. U.S. Pat. No. 4,847,265 also describes various other salts of Clopidogrel base as well as of the dextrorotatory isomer like its hydrochloride, carboxylic acid and sulfonic acids salts were prepared. Specifically salts of acetic, benzoic, fumaric, maleic, citric, tartaric, gentisic, methanesulfonic, ethanesulfonic, benzenesulfonic and lauryl sulfonic acids were prepared. However, according to the patent, these salts usually precipitated in amorphous form and/or they were hygroscopic making them difficult to handle in an industrial scale. Also, no process and no data corresponding to any of these salts are reported. The specification also describes salts of dobesilic acid (m.p.=70° C.) and para-toluenesulfonic acid, having a melting point of 51° C., the purification of which, as accepted in the patent, proved to be difficult.

Clopidogrel besylate which is at least partly in crystalline (solvated) forms have been disclosed by Helm in their published applications WO2004072084 (US20050256152, EP 1480985 B1) and WO2004072085. Subsequently, Helm disclosed non-solvated forms in their application no. US20050203122.

We have disclosed new polymorphic forms of Clopidogrel mesylate, Clopidogrel besylate and Clopidogrel tosylate in our published Application No. WO 2004106344, which are stable, free flowing, scalable, useful industrially and have important pharmacological properties. We herein disclose improved processes for preparing different forms of (S)-(+) Clopidogrel besylate.

EMBODIMENT(S) OF THE PRESENT INVENTION

In an embodiment of the present invention is disclosed improved processes for the preparation of different forms of (S)-(+) Clopidogrel besylate.

In a further embodiment of the present invention is provided improved processes for the preparation of crystalline (S)-(+) Clopidogrel besylate.

In a still further embodiment is provided improved processes for the preparation of amorphous (S)-(+) Clopidogrel besylate.

As a further embodiment of the present invention are provided pharmaceutical compositions containing and the use of the various forms of (S)-(+) Clopidogrel besylate prepared according to the processes described herein.

These processes are easy to scale up, commercially viable, safe, easy to handle and provides operational simplicity.

DISCLOSURE OF INVENTION

The present invention discloses improved processes for the preparation of different forms (both amorphous and crystalline) of (S)-(+) Clopidogrel besylate.

The term Clopidogrel base, Clopidogrel besylate used in the specification means (S)-(+)-Clopidogrel base and (S)-(+)-Clopidogrel besylate respectively.

The amorphous form described in the specification is prepared by the process described below.

Clopidogrel base in suitable solvents is treated with benzene sulfonic acid, the solvent is evaporated to dryness and amorphous form is separated. Suitable solvents is selected from tetrahydrofuran (THF), methyl isobutyl ketone and the like or mixtures thereof.

The crystalline form of (S)-(+)-Clopidogrel besylate is prepared by any of the processes described below, or suitable combinations of one or more of any of the processes described below:

i) Clopidogrel base in suitable solvents is treated with benzene sulfonic acid and the solvent is removed to obtain the crystalline form. Suitable solvent(s) may be selected from methyl tertiary butyl ether, or suitable alcohols selected from $C_2$-$C_{12}$ alcohols which may be linear or branched, primary, secondary or tertiary alcohols such as ethanol, propanol, isopropanol, 1-butanol, 2-butanol, isobutanol, t-butanol, 1-pentanol, 1-hexanol, 2-hexanol, 3-hexanol, isohexanol, 1-heptanol, 2-heptanol, 3-heptanol, 4-heptanol, octanol, isooctanol, decanol, dodecanol and the like or mixtures thereof.

ii) Amorphous (S)-(+)-Clopidogrel besylate is dissolved in suitable solvents and the solvent is removed to obtain the crystalline form. Suitable solvent(s) may be selected from methyl tertiary butyl ether or suitable alcohols selected from $C_2$-$C_{12}$ alcohols which may be linear or branched, primary, secondary or tertiary alcohols such as ethanol, propanol, isopropanol, 1-butanol, 2-butanol, isobutanol, t-butanol, 1-pentanol, 1-hexanol, 2-hexanol, 3-hexanol, isohexanol, 1-heptanol, 2-heptanol, 3-heptanol, 4-heptanol, octanol, isooctanol, decanol, dodecanol and the like or mixtures thereof.

iii) Clopidogrel base in suitable solvents is treated with benzene sulfonic acid, the solution is seeded with crystals of (S)-(+)-Clopidogrel besylate and the solvent is removed to obtain the crystalline form. Suitable solvent(s) may be selected from methyl tertiary butyl ether or suitable alcohols selected from $C_2$-$C_{12}$ alcohols which may be linear or branched, primary, secondary or tertiary alcohols such as ethanol, propanol, isopropanol, 1-butanol, 2-butanol, isobutanol, t-butanol, 1-pentanol, 1-hexanol, 2-hexanol, 3-hexanol, isohexanol, 1-heptanol, 2-heptanol, 3-heptanol, 4-heptanol, octanol, isooctanol, decanol, dodecanol and the like or mixtures thereof.

iv) Amorphous (S)-(+)-Clopidogrel besylate is dissolved in suitable solvent(s) and the solution is seeded with crystals of (S)-(+)-Clopidogrel besylate. The solvent is removed to obtain the crystalline form. Suitable solvent(s) may be selected from methyl tertiary butyl ether or suitable alcohols selected from $C_2$-$C_{12}$ alcohols which may be linear or branched, primary, secondary or tertiary alcohols such as ethanol, propanol, isopropanol, 1-butanol, 2-butanol, isobutanol, t-butanol, 1-pentanol, 1-hexanol, 2-hexanol, 3-hexanol, isohexanol, 1-heptanol, 2-heptanol, 3-heptanol, 4-heptanol, octanol, isooctanol, decanol, dodecanol and the like or mixtures thereof.

Alternatively, the processes described above can be repeated by using the Clopidogrel base prepared according to the improved processes described by the applicant in U.S. Pat. No. 6,635,763.

The amorphous Clopidogrel benzene sulfonate (Clopidogrel besylate) prepared according to the process of the present invention has a melting point in between the range of 85° C.-95° C.

The crystalline Clopidogrel benzene sulfonate (Clopidogrel besylate) prepared according to the process of the present invention has a melting point in between the range of 130° C.-135° C.

The following non-limiting examples illustrate the inventor's improved processes for the preparation of different forms of (S)-(+) Clopidogrel besylate discussed in the invention and should not be construed to limit the scope of the invention in any way.

EXAMPLE 1

Preparation of Amorphous Clopidogrel Besylate

Clopidogrel base was dissolved in THF. To it, benzene sulfonic acid was added at 20° C., and the reaction mixture was heated to reflux temperature for 2 to 10 hr. The solvent was evaporated to dryness under reduced pressure to obtain Clopidogrel besylate, which on characterization showed to be the amorphous form.

The above process for preparing amorphous Clopidogrel besylate is carried out using methyl isobutyl ketone and the like or mixture of THF and methyl isobutyl ketone as a solvent.

EXAMPLE 2

Preparation of Crystalline Clopidogrel Besylate

Clopidogrel base (10 g) was dissolved in decan-1-ol at 50-55° C. To this, benzene sulfonic acid (5 g) was added at 50-55° C. and the reaction mixture was stirred for about 20 hr. The solid was filtered and washed with methyl tertiary butyl ether and dried in vacuum oven for at least 20 hr., to give Clopidogrel besylate, which on characterization was found to be crystalline form. M.P. 130-135° C.

EXAMPLE 3

Preparation of Crystalline Clopidogrel Besylate

Clopidogrel base (10 g) was dissolved in decan-1-ol at 50-55° C. To this, benzene sulfonic acid (5 g) was added at 50-55° C. The reaction mixture was seeded with crystalline Clopidogrel besylate and the reaction mixture was stirred for about 10 hr. The solid was filtered and washed with methyl tertiary butyl ether dried in vacuum oven for at least 20 hr. to give Clopidogrel besylate, which on characterization was found to be crystalline form.
M.P. 130-135° C.

EXAMPLE 4

Preparation of Crystalline Clopidogrel Besylate

Clopidogrel base (60 g) was dissolved in isopropanol at 50-55° C. To it was added benzene sulfonic acid (30 g) dissolved in isopropanol at 50-55° C. The reaction mixture was stirred for 20 hr. The solid was filtered and washed with isopropanol and dried in a vacuum oven for at least 20 hr. to give Clopidogrel besylate, which on characterization was found to be crystalline form, M.P. 130-135° C.

EXAMPLE 5

Preparation of Crystalline Clopidogrel Besylate

Clopidogrel base (30 g) was dissolved in isopropanol at 50-55° C. To this mixture benzene sulphonic acid (15 g) was added at 50-55° C. The reaction mixture was stirred for 20 hr. The solid was filtered and washed with cold isopropanol and dried in a vacuum oven for at least 20 hr. to give Clopidogrel besylate, which on characterization was found to be crystalline form. M.P. 130-135° C.

EXAMPLE 6

Preparation of Crystalline Clopidogrel Besylate

Clopidogrel base (10 g) was dissolved in decan-1-ol at 50-55° C. To this, benzene sulfonic acid (5 g) dissolved in decan-1-ol was added at 50-55° C. The reaction mixture was seeded with crystalline Clopidogrel besylate and the reaction mixture was stirred for about 20 hr. The solid was filtered and washed with methyl tertiary butyl ether and dried in vacuum oven for at least 20 hr. to give Clopidogrel besylate, which on characterization was found to be crystalline form. M.P. 130-135° C.

EXAMPLE 7

Preparation of Crystalline Clopidogrel Besylate

Clopidogrel base (100 g) was dissolved in decan-1-ol at 50-55° C. To this, benzenesulfonic acid (50 g) dissolved in decan-1-ol was added at 50-55° C. The reaction mixture was seeded with crystalline Clopidogrel besylate (1 g) and the reaction mixture was stirred for about 10 hr. The solid was filtered and washed with methyl tertiary butyl ether and dried in vacuum oven for at least 20 hr. to give Clopidogrel besylate, which on characterization was found to be crystalline form. M.P. 130-135° C.

EXAMPLE 8

Preparation of Crystalline Clopidogrel Besylate

Clopidogrel base (5 g) was dissolved in methyl tertiary butyl ether. To this, benzene sulfonic acid (2.5 g) dissolved in methyl tertiary butyl ether was added at 50-55° C. The reaction mixture was seeded with crystalline Clopidogrel besylate (50 mg) and the reaction mixture was stirred for at least 24 hr. The solid was filtered and washed with methyl tertiary butyl ether and dried in vacuum oven for at least 20 hr. to give Clopidogrel besylate, which on characterization was found to be crystalline form.
M.P. 130-135° C.

EXAMPLE 9

Preparation of Crystalline Clopidogrel Besylate

Clopidogrel base (100 g) was dissolved in isopropanol at 50-55° C. To this, benzene sulfonic acid (50 g) dissolved in isopropanol was added at 50-55° C. The reaction mixture was seeded with crystalline Clopidogrel besylate (1 g) and the reaction mixture was stiffed for about 10 hr. The solid was filtered and washed with isopropanol and dried in vacuum oven for at least 20 hr. to give Clopidogrel besylate, which on characterization was found to be crystalline form. M.P. 130-135° C.

EXAMPLE 10

Preparation of Crystalline Clopidogrel Besylate

Clopidogrel base (100 g) was dissolved in isopropanol at 50-55° C. To this, benzene sulfonic acid (50 g) was added at 50-55° C. The reaction mixture was seeded with crystalline Clopidogrel besylate (1 g) and the reaction mixture was stirred for about 10 hr. The solid was filtered and washed with isopropanol and dried in vacuum oven for about 20 hr. to give Clopidogrel besylate, which on characterization was found to be crystalline form. M.P. 130-135° C.

EXAMPLE 11

Preparation of Crystalline Clopidogrel Besylate

Clopidogrel base (30 g) was dissolved in hexan-1-ol at 50-55° C. To this, benzene sulfonic acid (15 g) dissolved in hexan-1-ol was added at 50-55° C. The reaction mixture was seeded with crystalline Clopidogrel besylate (1 g) and the reaction mixture was stirred for about 10 hr. The solid was filtered and washed with methyl tertiary butyl ether and dried in vacuum oven for at least 20 hr. to give Clopidogrel besylate, which on characterization was found to be crystalline form. M.P. 130-135° C.

The besylate salts of Clopidogrel prepared according to the processes of the present invention can be administered to a person in need of it either without further formulation, or formulated into suitable formulations and dosage forms as are well known.

Some of the advantages of the processes for preparation of different forms of Clopidogrel besylate according to the present invention are:

scalable at plant level and so industrially useful
easy to operate
good recovery of solvents
gives high yield

The invention claimed is:

1. A process for the preparation of crystalline form of (S)-(+)-Clopidogrel besylate comprising:
    i. treating Clopidogrel base with benzene sulfonic acid in solvent(s) selected from the group consisting of $C_6$-$C_{12}$ alcohols which may be linear or branched, primary, secondary or tertiary alcohols and mixtures thereof to form a reaction mixture and
    ii. removing the solvent to obtain the crystalline form.

2. A process for the preparation of crystalline form of (S)-(+)-Clopidogrel besylate as claimed in claim 1, wherein the reaction mixture is seeded with crystals of (S)-(+)-Clopidogrel besylate.

* * * * *